United States Patent [19]

Ghommidh et al.

[11] 4,366,183
[45] Dec. 28, 1982

[54] PROCESS FOR MAKING BIOACTIVE COATINGS ON OSSEOUS PROSTHESES, AND PROSTHESES THUS OBTAINED

[75] Inventors: Josette Ghommidh, Castanet Tolosan; Bernard Buttazzoni, Marseilles; Georges Constant, Ramonville St. Agne; Etienne Diloy; Roland Morancho, both of Toulouse, all of France

[73] Assignee: Societe Europeene de Propulsion, Puteaux, France

[21] Appl. No.: 272,129

[22] Filed: Jun. 10, 1981

[30] Foreign Application Priority Data

Jun. 17, 1980 [FR] France .............................. 80 13433

[51] Int. Cl.³ .......................... A61F 1/24; A61C 13/30
[52] U.S. Cl. ............................................. 427/2; 3/1.9
[58] Field of Search ............................. 3/1.9; 427/214

[56] References Cited

U.S. PATENT DOCUMENTS 3,918,100 11/1975 Shaw ...................................... 3/1.91
3,984,914 10/1976 Schwartz ................................ 3/1.9
4,223,412 9/1980 Aoyagi .................................... 3/1.9

FOREIGN PATENT DOCUMENTS 2659591 7/1977 Fed. Rep. of Germany .......... 3/1.9
2708917 9/1978 Fed. Rep. of Germany .......... 3/1.9
863098 of 0000 United Kingdom .
1530670 of 0000 United Kingdom .
1550575 of 0000 United Kingdom .

*Primary Examiner*—Sam Silverberg
*Attorney, Agent, or Firm*—Jeffery, Schwaab, Mack, Blumenthal & Koch Schwartz

[57] ABSTRACT

The present invention relates to a process for making bioactive coatings on osseous prostheses, wherein, from solutions, a mist of particles containing calcium ions and orthophosphate ions is made and said mist is brought into contact with an implant made of inert material under such operational conditions that at least one desired calcium phosphate is formed by reaction on the hot surface of said inert implant, and to the osseous implants obtained by this process.

3 Claims, 1 Drawing Figure

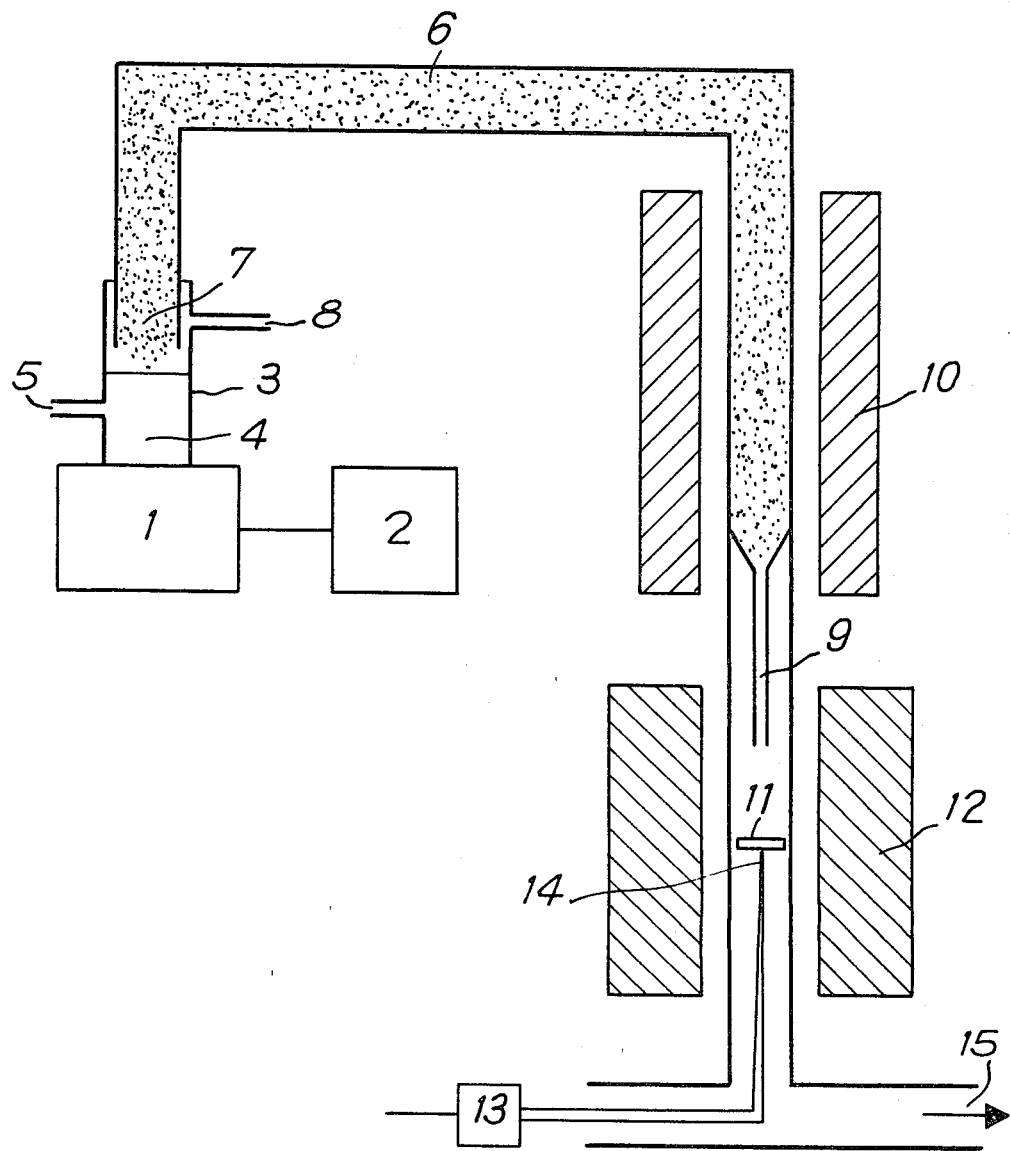

PROCESS FOR MAKING BIOACTIVE COATINGS ON OSSEOUS PROSTHESES, AND PROSTHESES THUS OBTAINED

The present invention relates to a process for making bioactive coatings on osseous prostheses and to the prostheses thus obtained.

Osseous prostheses (such as articular prostheses and dental implants) used at present comprise a part adapted to be permanently fixed in the compact or spongy bone or in a cavity of the bone. To hold these prostheses in place, either a cement interposed between the prosthesis and the bone is used, or a mechanical anchoring by force-fitting the prosthesis in a cavity whose wall has been rendered rough; in the latter case, the development of the bone, after the prosthesis has been placed in position, provokes a reinforcement of the anchoring of the prosthesis without there being any weld between the bone and the prosthesis.

Furthermore, it is known that certain mineral solids participate in the physiological mechanisms of living beings; phosphates of calcium, and more particularly apatites, are solid compounds which are formed at the calcified tissues (bones and teeth) of vertebrates. These biological compounds fulfill two functions, a mechanical one (resistance to efforts) and a physiological one (metabolism of the phosphorus and calcium). Certain relations have recently been discovered at the interface between an implant whose surface is provided with phosphate (or phosphates) of calcium and the adjacent bone in the form of a veritable biochemical weld between the bone and the implant. Thus, it is known that the tricalcium phosphate $\beta$ may be "assimilated" by the osseous tissue and replaced by said tissue; it is also known that calcium hydroxyapatite (particularly if it has a certain calcium deficiency) has a crystalline structure very close to the osseous structure and may consequently serve as receiving structure with respect to a development of the bone; finally, it is known that, with respect to an adjacent osseous structure, $\gamma$ or $\beta$ pyrophosphate (mainly $\gamma$ pyrophosphate) plays an important role in the connection (adhesion) between the osseous structure and the implant. It is therefore important for a technique to be available allowing the deposit, on the surface of an implant base made of inert material, of a bioactive coating based on phosphate of calcium or a mixture of suitably chosen phosphates of calcium. This is the purpose of the invention.

Thus, according to the present invention, a thin bioactive coating of phosphate (or phosphates) of calcium is made on an implant made of an inert material so as to promote biochemical welding between the bone and the implant thus coated.

The inert material used for making the base of the implant may be a metal alloy (stainless steel—surgical quality), a cobalt-chromium-nickel-molybdenum alloy, an alloyed titanium, a polymer, ceramic, carbonaceous material (carbon fibres), etc.. These latter materials (carbon fibres—pyrocarbon matrix in particular) are particularly advantageous due on the one hand to the intrinsic biocompatibility of the carbon with respect to the osseous tissue and, on the other hand, to the bioflexibility of these materials, this bioflexibility being the property of said materials of having a modulus of elasticity close to that of the bone.

Thus, according to the invention, a thin bioactive coating based on a phosphate of calcium is made on an implant of inert material. Among the phosphates of calcium which may be used according to the invention, mention will be made of apatites, hydroxyapatites, tricalcium $\beta$ phosphate, calcium pyrophosphate $\gamma$ and $\beta$, brushite or monetite. These calcium phosphates are used alone or mixed together, in an armorphous, partially crystalline or cyrstalline form and they may comprise other materials (for example metal ions or other mineral compounds) which will be capable of improving their properties (for example adhesiveness on the inert material or the surface properties).

The bioactive coating must be thin, i.e. it must have a thickness of between 2 and 15 $\mu$m, so as to perform a role which is as beneficial as possible (catching and assimilation) with respect to the bone with which it is placed in contact.

The process according to the invention for making the thin bioactive coating, based on calcium phosphate, on the inert implant is characterised in that, from aqueous solutions containing a phosphate of calcium, such as a dicalcium phosphate, a mist of water particles containing said phosphate is made, said mist is entrained with the aid of a suitable gaseous current and said gaseous current is oriented on the implant to be coated whilst said current and said implant are heated to a suitable temperature to provoke the chemical transformation of said phosphate of calcium contained in the starting aqueous solution into at least one bioactive phosphate of calcium.

The starting aqueous solution is preferably a hydrated dicalcium phosphate solution of formula $CaHPO_4, 2H_2O$. The aqueous solution will preferably comprise as large a quantity of this hydrated dicalcium phosphate as possible, i.e. it will be close to concentration of saturation (at ordinary temperature) of said dicalcium phosphate. (The optimal concentration will thus be of the order of 120 mg of phosphate per liter of solution).

From this solution, a mist (i.e. the fractioning of said solution into fine droplets) is made by any device. A pneumatic atomizer or a resonant cavity, or a piezoelectric transducer may be used. The droplets of said mist advantageously have diameters of the order of 5 to 50 or 100 $\mu$m, although this is not limiting.

The droplets of said mist are entrained by a vector gas such as nitrogen, argon, air, so as to be brought into contact with the implant to be coated. Experience proves that it is desirable to take steps (heating) to avoid condensation of these droplets on the walls of the tubes in which they are entrained and to provide a specific orientation of the current of droplets towards said implant to promote the real contact between said droplets (or the dried products that they contain) with the surface of said implant.

The droplets entrained by the current of carrier gas are sent into an oven whose temperature is between 100° and 350° C., then onto the surface of the implant which is at a temperature of between 150° and 600° C. In the course of heating the droplets, a more or less complete vaporization of the water of these droplets is, on the one hand, produced, and, on the other hand, in liquid phase, a hydrolysis is produced, producing, at least partially, the deposited bioactive phosphate; this transformation of the dicalcium phosphate found in the water in a more or less ionic form into one (or more) bioactive phosphate deposited on the surface of the substrate is carried out, depending on the experimental conditions, either before the deposit of the phosphate on the implant or, most often, at the moment of contact of the particles (droplets or solid particles) with the surface of the substrate. This reaction at the moment of the contact between the particles and the surface encountered apparently explains the fact that the nature of the material which is formed on the surface appears to depend on the nature of this surface.

In one of the preferred embodiments of the invention, the gaseous current comprising the droplets and the implant are heated in the same oven to a temperature of between 150° and 350° C.; moreover, the duration of the passage of the droplets in the oven is controlled so that the evaporation of the water of said droplets is total before these droplets arrive on the surface of the implant.

The pressure at which the yield of the implant is effected is generally equal to atmospheric pressure. However, it may be advantageous, particularly to accelerate the chemical transformations within the droplets and to increase the yield, to operate at a pressure higher than atmospheric pressure.

As has been indicated hereinabove, the process is particularly suitable for making layers of hydroxyapatite, tricalcium phosphate $\beta$, pyrophosphate of calcium $\gamma$ and $\beta$, brushite and monetite, alone or mixed, depending on the operating conditions, but also for making multiple layers by modifying the operational parameters in the course of elaboration; due to the possibility of choosing the operational conditions, and taking into account the nature of the implant and the subsequent necessities of use, deposits may be made containing determined proportions of such or such bioactive and/or inert phosphate. In particular, it has been possible to make deposits formed (or containing) hydroxyapatite deficient in calcium which, according to present knowledge, constitutes the material whose structure is closest to the structure of the bone.

The substrate may be chosen from a very large number of materials, taking into account the temperature of deposit: stainless steels, special refractory steels, pure or alloyed titanium, composite carbon-carbon materials.

Having set forth the process of the invention in its general form, the following description furnishes several embodiments for illustrating said process; these examples were carried out by means of an apparatus of the type shown schematically in the single FIGURE and which is previously described hereinafter with reference to this FIGURE.

This apparatus essentially comprises:
an ultrasonic generator 1 supplied electrically at 2;
a recipient 3 containing the liquid 4 to be atomized, flanked by a liquid intake pipe 5;
a conduit 6 for conveying the mist 7 bearing at the beginning the intake pipe of the vector gas 8 and, at the outlet, a nozzle 9 which is for example at a distance of 10 to 70 mm from the substrate (implant) 11; in the final part, this conduit is pre-heated by system 10;
the substrate (implant) 11, heated by the oven 12 to the temperature set by a regulation system 13 and its thermocouple 14;
an evacuation 15 for the mist not having reacted, the vector gas and the products of decomposition, The modus operandi for making a deposit comprises the following steps:
preparation of the solution to be atomized and placing in the recipient 3;
introduction of the substrate 11 in the oven 12;
scavenging of the conduit 6 by the vector gas and adjustment of its rate of flow;
heating of the oven 12;
switching on of the pre-heating system 10;
switching on of the ultrasonic generator 1 and adjustment of the power used;
at the end of the experimentation, the ultrasonic generator, the heating of the oven 12 and of the pre-heating device 10 are successively stopped; the circulation of the vector gas is stopped when the temperature of the oven has dropped to below 80° C.

This apparatus and modus operandi have, of course, been given solely by way of illustration.

Several examples of deposit made are indicated hereinbelow.

EXAMPLE 1

Deposit of calcium hydroxyapatite

The starting aqueous solution is made by dissolving 120 mg of hydrated dicalcium phosphate ($CaHPO_4$, $2H_2O$) in 1 liter of distilled water. Chemical atomization is carried out for 4 hours with a rate of flow of 6 liters/minute of nitrogen, the substrate constituted by a plate of composite carbon-carbon material being heated to 350° C., the temperature of the pre-heating being 300° C.

A white crystalline layer of calcium hydroxyapatite is observed at the end of the experiment on the substrate. The nature of this layer was identified by X-ray diffraction and by observation of the secondary emissions in an electron beam with an apparatus of "E.D.A.X." type. The thickness of this layer measured by electronic scanning microscopy is, in this example, about 4 $\mu$m.

EXAMPLE 2

Deposit of calcium hydroxyapatite

The conditions of this experimentation are the same as in 1, except for the vector gas which is constituted by argon under the same conditions of rate of flow. The results are identical.

EXAMPLE 3

Deposit of calcium hydroxyapatite

The conditions of this experimentation are the same as in 1, except for the starting solution prepared from calcium hydroxide and phosphoric acid, the relative quantities of phosphoric acid and of hydroxide corresponding substantially to tricalcium phosphate. A deposit of calcium hydroxyapatite is thus made.

EXAMPLE 4

Deposit of calcium hydroxyapatite

The conditions of this experiment are the same as in 1, except for:
the temperature of the substrate which is 300° C.,
the rate of flow of the vector gas which is 8 liters/minute.

The total duration of the deposit was 8 hours.

The deposited layer is calcium hydroxyapatite; its thickness is about 7 $\mu$m.

The deposits of hydroxyapatite are products of formula $Ca_{10}(PO_4)_6(OH)_2$.

EXAMPLES 5 and 6

Under the same conditions as those described in Examples 1 to 4, but varying the rate of flow of the starting solution, deposits may be obtained containing, apart from hydroxyapatite, either anhydrous dicalcium phosphate or γ-pyrophosphate, or a mixture of these two products.

An increase of the temperature of the support (towards 400° C.) also enables a γ-pyrophosphate phase to be obtained in the deposit.

Finally, it has been noted that the extension of the duration of the deposits makes it possible, all else being equal, to modify the nature of the deposit (for example by formation of pyrophosphate, then hydroxyapatite) not by a chemical transformation of the deposits already made, but by the deposits being effected on surfaces whose nature varies in the course of the duration of the test.

EXAMPLE 7

Deposit of γ form calcium pyrophosphate

The conditions of this experiment are the same as in 4, except for:

the temperature of the substrate which is 400° or 500° C., the duration of circulation of the mist on the substrate which is 3 hours.

The deposited layer is constituted by γ form calcium pyrophosphate with a thickness of about 3 μm.

EXAMPLE 8

Deposit of β form calcium phyrophosphate

The conditions of this experiment are the same as in 7, except for the temperature of the substrate which is 600° C.

The deposited layer is constituted by β form calcium pyrophosphate with a thickness of about 3 μm.

The temperature therefore strongly influences the nature of the deposit.

EXAMPLE 9

Deposit of monetite

The conditions of this experimentation are the same as in 1, with the exception of:

the temperature of the substrate which is 400° C., the rate of flow of the vector gas which is 5 liters/minute the temperature of the pre-heating system which is 100° C.

The deposited layer is constituted by monetite CaHPO$_4$ of thickness of about 2.5 μm.

This experiment shows the influence of pre-heating.

EXAMPLE 10

Deposit of calcium hydroxyapatite

The conditions of this experiment are the same as in 1, except for:

the substrate which is a plate of polytetrafluoroethylene, the temperature of the substrate which is 250° C., the pre-heating temperature which is 200° C.

The deposited layer, of about 4 μm, is constituted by calcium hydroxyapatite and traces of γ-pyrophosphate of calcium.

EXAMPLE 11

Deposit of monetite

The conditions of this experimentation are the same as in 10, except for the substrate which is made of fritted alumina.

The deposited layer is monetite, showing that the deposits may also be made on ceramics, but with an influence of the substrate on the nature of the deposit.

EXAMPLE 12

Deposit of monetite

The conditions of this experiment are the same as in 10, except for the substrate which is made of stainless steel 18/8.

The deposited layer is monetite showing that metals may also be used as substrate.

EXAMPLE 13

Deposit of calcium hydroxyapatite and γ-pyrophosphate of calcium, mixed

The conditions of this experiment are the same as in 1, except for:

the composition of the starting aqueous solution which is obtained by dissolving 180 mg of hydrated monocalcium phosphate CaH$_4$(PO$_4$)$_2$, H$_2$O in one liter of distilled water, the temperature of the substrate which is 300° C., the pre-heating temperature which is 280° C., the rate of flow of the vector gas which is 5 liters/minute.

The deposited layer is a mixture of calcium hydroxyapatite and of calcium γ-pyrophosphate, the latter compound being preponderant.

What is claimed is:

1. A process for applying thin bioactive coatings to an osseous prostheses support comprising the steps of:

producing a mist of droplets of a concentrated liquid solution of a phosphate of calcium;

entraining said mist in a gaseous current;

heating said support to a temperature from 200° to 600° C., directing said gaseous current containing said mist onto the heated support, heating the mist to a temperature from 100° to 350° C. by contact with the hot support and vaporizing the liquid from said liquid solution to deposit a coating of calcium phosphate material on said support, said phosphate material initially present in the liquid solution being transformed into at least one bioactive phosphate selected from the group consisting of hydroxyapatite, beta-form tricalcium phosphate, gamma- and beta-form calcium pyrophosphate, brushite, monetite and mixtures of one or more of the foregoing; and maintaining the operational conditions of said deposition such that the thickness of the deposited coating is from 2 to 15 micrometers.

2. A process according to claim 1, wherein said liquid is water.

3. A process according to claim 1, wherein said phosphate of calcium is dicalcium phosphate.

* * * * *